United States Patent
Bordat et al.

(10) Patent No.: US 6,379,681 B1
(45) Date of Patent: Apr. 30, 2002

(54) OIL-IN-WATER EMULSIONS FOR RECONSTITUTING LAMELLARITY OF THE LIPID STRUCTURE OF DAMAGED SKIN

(75) Inventors: Pascal Bordat, Flourens (FR); Stephanie Ortanderl, Juechen (DE); Martina Kampmann, Korschenbroich (DE); Marianne Waldmann-Laue, Monheim (DE); Georg Knuebel, Duesseldorf (DE); Marcus Mausberg, Solingen (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/402,301

(22) PCT Filed: Nov. 28, 1997

(86) PCT No.: PCT/EP97/06639

§ 371 Date: Jan. 13, 2000

§ 102(e) Date: Jan. 13, 2000

(87) PCT Pub. No.: WO98/44896

PCT Pub. Date: Oct. 15, 1998

(30) Foreign Application Priority Data

Apr. 3, 1997 (DE) .......................................... 197 13 793

(51) Int. Cl.[7] .............................. A61K 7/00; A61K 7/48; B01F 17/28
(52) U.S. Cl. ...................... 424/401; 424/455; 514/938; 252/356
(58) Field of Search ................................ 424/401, 455; 514/938; 252/356

(56) References Cited

U.S. PATENT DOCUMENTS

| 4,400,295 A | * 8/1983 | Ootsu et al. ............... 252/356 |
| 4,767,625 A | 8/1988 | Mitsuno et al. ............... 424/95 |
| 5,658,575 A | 8/1997 | Ribier et al. ................ 424/401 |
| 5,851,543 A | * 12/1998 | Korb et al. .................. 424/401 |
| 6,133,463 A | * 10/2000 | Fourneron et al. ............ 554/79 |

FOREIGN PATENT DOCUMENTS

| DE | 43 37 041 | 5/1995 |
| EP | 0 217 105 | 4/1987 |
| EP | 0 312 343 | 4/1989 |
| EP | 0 641 557 | 3/1995 |
| WO | WO94/17830 | 8/1994 |
| WO | WO95/28913 | 11/1995 |
| WO | WO98/07406 | 2/1998 |

OTHER PUBLICATIONS

Derwent Patent Abstract (WPAT) No. 1995–099980[14].

Derwent Patent Abstract (WPAT) No. 1987–095199[14].

Derwent Patent Abstract (WPAT) No. 1995–171245[23].

Cosmetics and Toiletries, vol.101, pp. 113–115 (1986).

Pharmaceutical Skin Penetration Enhancement, pp. 269–291 (1993).

* cited by examiner

Primary Examiner—Diana Dudash
Assistant Examiner—M. Haghighatian
(74) Attorney, Agent, or Firm—Stephen D. Harper; Kimberly R. Hild; Glenn E. J. Murphy

(57) ABSTRACT

The present invention relates to a skin lightening composition comprising (a) a safe and effective amount of a compound of formula (I): wherein Z is Oxygen or Sulfur, (b) an average polarity solvent, (c) a polyhydric alcohol, (d) a solid fatty alcohol, (e) a nonionic surfactant, (f) water, and (g) lecithin wherein at least a portion of the above components (a), (b), (c), (d), (e), (f) and (g) forms a liquid crystal.

6 Claims, No Drawings

OIL-IN-WATER EMULSIONS FOR RECONSTITUTING LAMELLARITY OF THE LIPID STRUCTURE OF DAMAGED SKIN

This application is filed under 35 U.S.C. 371 and based on PCT/EP97/06639, filed Nov. 18, 1997.

BACKGROUND OF THE INVENTION

1. Field of the Invention

This invention relates to so-called lamellar emulsions of which the emulsion droplets are surrounded by a liquid-crystalline lamellar phase of lipid molecules and water and are thus particularly stabilized and which are particularly suitable for restoring the disturbed degree of order of damaged skin.

2. Discussion of Related Art

It is known from the technical literature that lamellar emulsions are capable of favorably influencing the water metabolism of the skin and of storing large amounts of moisture in the skin. According to G. Dahms, Cosmetics & Toiletries, Vol. 101, November 1986, pages 113–115, lamellar emulsions can be produced by using an oil with an emulsifier of similar structure. EP-A-0 641 557 recommends the use of a lipophilic surfactant, a hydrophilic surfactant and a free fatty acid as emulsifier components. According to WO 94/17830, sorbitan and sucrose fatty acid esters are used as emulsifiers while, according to WO 95/28913 A1, urea is additionally used for the production of lamellar emulsions.

It has now been found that it is not so much the nature of the oil or emulsifier as the choice of a suitable co-emulsifier which is crucial to the production of oil-in-water emulsions containing anisotropic lamellar phases.

DESCRIPTION OF THE INVENTION

Accordingly, the present invention relates to an oil-in-water emulsion with lamellar liquid crystalline phases containing a cosmetic oil or fatty component, a hydrophilic emulsifier and a lipophilic co-emulsifier, characterized in that the lipophilic co-emulsifier used is a lipid corresponding to the general formula $R^1$—O—$R^2$, where $R^1$ is a primary linear alkyl, alkenyl or acyl group containing 20 to 30 carbon atoms and $R^2$ is hydrogen, a group with the formula —$(C_nH_{2n}O)_x$—H, where x=1 or 2 and n=2–4, or a polyhydroxyalkyl group containing 4 to 6 carbon atoms and 2 to 5 hydroxyl groups.

The oil-in-water emulsions according to the invention may contain either a cosmetic oil or fatty component or a water-in-oil emulsion as the inner phase. In the latter case, the lamellar emulsions according to the invention are water-in-oil-in-water emulsions.

The lipophilic co-emulsifier $R^1$—O—$R^2$ is preferably a behenic or erucyl derivative, in which $R^1$ is a linear terminally substituted alkyl, alkenyl or acyl group containing 22 carbon atoms, in a quantity of 10 to 90% by weight of the oil phase. In a particularly preferred embodiment, behenyl alcohol is present as the lipophilic co-emulsifier in a quantity of 20 to 80% by weight, based on the oil phase as a whole.

Other suitable co-emulsifiers are products of the addition of 1 or 2 moles of ethylene oxide or propylene oxide onto behenyl alcohol, erucyl alcohol, arachidyl alcohol or even onto behenic acid or erucic acid. Finally, other suitable co-emulsifiers are the monoesters of $C_{20-30}$ fatty acids with polyols such as, for example, pentaerythritol, trimethylol propane, diglycerol, sorbitol, glucose or methyl glucose, Examples of such products are, for example, sorbitan monobehenate or pentaerythritol monoerucate.

Suitable hydrophilic emulsifiers for the production of the oil-in-water emulsions according to the invention are any surfactants suitable for the emulsification of cosmetic oil and fatty components. These are, above all, ionic emulsifiers or nonionic emulsifiers with an HLB value of 8 to 18. The HLB value is a value which can be calculated from the structure of the molecule in accordance with the equation HLB=0.2× (100 −L) where L is the percentage by weight of the lipophilic alkyl, alkenyl or acyl groups in the molecule.

Suitable ionic emulsifiers are anionic, cationic, zwitterionic and amphoteric surfactants, preferably those containing a primary linear $C_{12-18}$ alkyl or alkenyl group. Suitable anionic emulsifiers are, for example, the salts of $C_{12-18}$ fatty acids, of sulfuric acid monoesters or phosphoric acid monoesters of $C_{12-18}$ fatty alcohols, of $C_{12-18}$ acyl isethionic acids, of $C_{12-18}$ alkane sulfonic acids or of $C_{12-18}$ acylamino acids. Cationic emulsifiers are, for example, cetyl trimethyl ammonium chloride or dimethoxyethyl hydroxyethyl methyl ammonium chloride. Suitable zwitterionic surfactants are, for example, betaine surfactants, such as stearamidopropyl dimethyl carboxymethyl ammonium betaine, while suitable amphoteric surfactants are, for example, cetyl aminopropionic acid or cocoamphocarboxyglycinate. Amine oxide surfactants are also suitable hydrophilic emulsifiers.

Suitable nonionic surfactants with HLB values of 8 to 18 are, in particular, products of the addition of ethylene oxide onto fatty acids, fatty alcohols, fatty acid alkanolamides, fatty acid monoglycerides, sorbitan fatty acid esters, methyl glucoside fatty acid esters or other lipids containing carboxyl, hydroxyl or amino groups; the percentage content of ethoxy groups formed should be at least 40% by weight. Other suitable nonionic surfactants are alkyl polyglucosides, sugar esters and polyglycerol fatty acid esters.

Suitable oil and fatty components are any vegetable, animal, mineral and synthetic oils, fats and waxes suitable for use on the human body for physiological and aesthetic reasons. Examples include paraffins, fatty acid esters of monohydric or polyhydric alcohols, for example triglycerides, fatty acid/fatty alcohol esters, fatty acid/ dicarboxylic acid/polyol polyesters, fatty alcohol/diol/ dicarboxylic acid polyesters, di-n-alkyl ethers, polyolefins or silicone oils. Liquid oils or mixtures of oils and waxes which are liquid at 20° C. are preferably used. Monoesters suitable as oil components are, for example, the methyl esters and isopropyl esters of fatty acids containing 12 to 22 carbon atoms such as, for example, methyl laurate, methyl stearate, methyl oleate, methyl erucate, isopropyl palmitate, isopropyl myristate, isopropyl palmitate, isopropyl stearate, isopropyl oleate. Other suitable monoesters are, for example, n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyidecyl stearate, 2-octyldodecyl palmitate, oleyl oleate, oleyl erucate, erucyl oleate and esters obtainable from technical aliphatic alcohols mixture. and technical aliphatic carboxylic acids, for example esters of saturated and unsaturated fatty alcohols containing 12 to 22 carbon atoms and saturated and unsaturated fatty acids containing 12 to 22 carbon atoms which are obtainable from animal and vegetable fats. Naturally occurring monoester or wax ester mixtures, as present for example in jojoba oil or in sperm oil, are also suitable.

Suitable dicarboxylic acid esters are, for example, di-n-butyl adipate, di-n-butyl sebacate, di-(2-ethylhexyl)-adipate, di-(2-hexyldecyl)-succinate and diisotridecyl azelate. Suitable diol esters (III) are, for example, ethylene glycol dioleate, ethylene glycol diisotridecanoate, propylene glycol di-(2-ethylhexanoate), butanediol diisostearate and neopentyl glycol dicaprylate.

Suitable fatty acid triglycerides are natural vegetable oils, for example olive oil, sunflower oil, soybean oil, peanut oil, rapeseed oil, almond oil, palm oil and even the liquid fractions of coconut oil or palm oil, and animal oils such as, for example, neat's foot oil, the liquid fractions of beef tallow or even synthetic triglycerides of the type obtained by esterifying glycerol with $C_{8-22}$ fatty acids, for example triglycerides of caprylic acid/capric acid mixtures, triglycerides of technical oleic acid or palmitic acid mixtures.

The oil-in-water emulsions of cosmetic oil or fatty components containing lamellar liquid crystalline phases according to the invention are produced by methods known per se using hydrophilic emulsifiers and lipophilic co-emulsifiers, the aqueous phase which may contain hydrophilic emulsifiers being intensively mixed with the oil or fatty phase which contains as lipophilic co-emulsifiers at least one lipid corresponding to the general formula $R^1$—O—$R^2$, where $R^1$ is a linear alkyl, alkenyl or acyl group containing 20 to 30 carbon atoms and $R^2$ is hydrogen, a group with the formula —$(C_nH_{2n}O)_x$—H, where x=1 or 2 and n=2–4, or a polyhydroxyalkyl group containing 4 to 6 carbon atoms and 2 to 5 hydroxyl groups.

The aqueous phase contains all the water-soluble components, for example a water-soluble emulsifier, the preservatives, buffer salts, magnesium chloride, propylene glycol, glycerol, water-soluble polymeric thickeners or water-soluble cosmetic active substances.

Besides the cosmetic oils and fats, the oil-soluble emulsifiers and, in particular, the lipophilic co-emulsifier are added to the oil phase. Finally, other oil-soluble auxiliaries optionally present, for example oil-soluble antioxidants or preservatives, waxes, silicones and the oil-soluble cosmetic active substances, are also added to the oil phase. The oil phase is then heated to a temperature at which it is present as a clear homogeneous melt. The aqueous phase is also heated to the same temperature. The oil phase and the water phase are then intensively mixed with one another.

Where a nonionic emulsifier with a phase inversion temperature below 100° C. is used, the emulsion is preferably prepared at that temperature or is heated to that temperature during emulsification. The emulsion thus becomes a water-in-oil emulsion which then inverts back into an o/w emulsion when the temperature falls below the phase inversion temperature and which accumulates in a particularly fine-droplet, low-viscosity and storage-stable form.

The addition of perfumes and particularly readily volatile or heat-sensitive substances is preferably carried out after cooling to temperatures of 40° C. or lower.

The lamellar emulsions according to the invention may be thinly liquid or cream-like according to the type and quantity of the inner phase. Their consistency can also be controlled to a certain extent by thickeners or by the emulsification process, i.e. through the droplet fineness.

The oil-in-water emulsions according to the invention retain their lamellarity irrespective of the ratio by weight of oil phase to water phase. In other words, the oil droplets retain their liquid crystalline lipid double layer shell even after heavy dilution with water. By virtue of their birefringent properties, they can be made visible in polarized light.

The lamellar emulsions according to the invention are suitable for skin care. Not only do they increase the moisture retention capacity of the skin, they also increase the degree of order of the epidermis and improve the barrier function of the skin. After skin damage, for example by surfactants or mechanical stressing, treatment with the lamellar cream according to the invention leads more quickly to restoration of the lamellarity of the epidermal lipid structures.

Accordingly, the present invention also relates to the use of an oil-in-water emulsion with lamellar liquid crystalline phases containing a cosmetic oil or fatty component, a hydrophilic emulsifier and a lipophilic co-emulsifier which is a lipid corresponding to the general formula $R^1$—O—$R^2$, where $R^1$ is a primary linear alkyl, alkenyl or acyl group containing 20 to 30 carbon atoms and $R^2$ is hydrogen, a group with the formula —$(C_nH_{2n}O)_x$—H, where x=1 or 2 and n=2–4, or a polyhydroxyalkyl group containing 4 to 6 carbon atoms and 2 to 5 hydroxyl groups, for restoring the lamellarity and degree of order of the epidermal lipid structures of damaged skin.

This effect of the lamellar oil-in-water emulsions according to the invention can be experimentally demonstrated by infrared-spectroscopic examination of the conformation order of the —$(CH_2)_x$—chains of the lipids of the stratum corneum. The position of the stretching vibrational bands $v_s(CH_2)$ and $v_{as}(CH_2)$ (ca. 2850 cm$^{-1}$ and 2915 cm$^{-1}$) is dependent on the percentage of higher-energy "gauche" conformers of a lipid chain as opposed to the lower-energy (all-trans) conformers. Increasing disorder of the lipid membrane leads to a displacement of these bands to higher frequencies (up to a few cm$^{-1}$) on account of the increase in the percentage of the higher-energy vibrations of the "gauche" conformers (cf. R. O. Potts, M. L. Francoeur: Infrared Spectroscopy of Stratum Corneum Lipids in: Pharmaceutical Skin Penetration Enhancement, ed. by Kenneth A. Walters, Jonathan Hadgraft, 1993, pages 269–291).

Using a piece of skin damaged by washing with lauryl sulfate solution, it can be shown that an increase in the conformation order ("lamellarity") of the epidermal lipids can be achieved in a few days by treatment with a lamellar cream according to the invention.

The following Examples are intended to illustrate the invention.

EXAMPLES

Creams with a Lamellar Structure

1. General Production Process

The oil and fatty components, emulsifiers, co-emulsifiers and the lipophilic auxiliaries were mixed and heated to 95° C.

The water-soluble auxiliaries (preservative, xanthan gum) were dissolved in water. The aqueous phase heated to 90° C. was emulsified while stirring into the fatty phase heated to 90° C. The emulsion formed was homogenized and at the same cooled to 40° C. After addition of the perfume oil, the emulsion was cooled with stirring to 20° C.

The following commercial products were used:

(1) Baysilonöl M 350: polydimethyl siloxane, 350 cst (25° C.

(2) Lanette® 22: technical behenyl alcohol ($C_{22}$:70–80%, $C_{20}$:10–20%, $C_{18}$:5–15%)

(3) Controx®KS: tocopherol/tallow fatty acid glyceride citrate mixture (4) Citricidal®: grapefruit seed extract (5) Dow Corning 344 Fluid: octamethyl cyclotetrasiloxane (6) Abil® Wax 9809: polysiloxanelpolyalkylene copolymer (7) Euxyl®K-400: 1,2-dibromo-2,4-dicyanobutane (8) Arlacel® 1689: polyglycerol/sorbitan fatty acid ester
(9) Biophilic® S: lecithin/fatty acid/fatty alcohol mixture
(10) Arlacel® 989: hydrogenated castor oil ethoxylate (7EO)
(11) Gilugel min: hydroxystearic acid Al/Mg salt/paraffin oil
(12) Glucolys® (Seporga): mixture of glucose, sorbitol and citric acid 2. Formulation Examples

TABLE I

|  | 1 | 2 | 3 | 4 | 5 | 6 | 7 |
|---|---|---|---|---|---|---|---|
| Oil Phase: | | | | | | | |
| Paraffin oil | — | — | 5.0 | 10.0 | 20.0 | — | — |
| Heptamethyl nonane | — | — | — | — | — | 10.0 | 10.0 |
| Di-n-octyl ether | — | — | 5.0 | 10.0 | 20.0 | — | — |
| Night light oil | 2.0 | 2.0 | — | — | — | — | — |
| Sunflower oil | — | — | — | — | — | 10.0 | 10.0 |
| Almond oil | — | 2.0 | — | — | — | — | — |
| Isopropyl isostearate | 3.0 | 3.0 | — | — | — | — | — |
| Cetearyl isononanoate | 2.0 | — | — | — | — | — | — |
| Baysilonol M350 | 0.5 | 0.5 | — | — | — | — | — |
| Tocopherol acetate | 0.5 | 0.5 | — | — | — | — | — |
| Lanette 22 | 6.0 | 6.0 | 6.0 | 6.0 | 6.0 | 6.0 | 6.0 |
| pHB propyl ester | — | — | — | — | — | 0.1 | 0.1 |
| Controx KS | 0.05 | 0.05 | 0.05 | 0.05 | 0.05 | 0.05 | 0.05 |
| Aqueous phase | | | | | | | |
| PEG 25 soyasterol | 0.5 | 0.5 | — | — | — | — | — |
| Na cetyl/stearyl sulfate | 0.24 | 0.24 | — | — | — | — | 0.1 |
| K cetyl hydrogen phosphate | — | — | 0.1 | 0.1 | 0.1 | 0.1 | — |
| Xanthan gum | 0.05 | 0.05 | 0.3 | 0.3 | 0.3 | 0.1 | 0.1 |
| Dipropylene glycol | 5.0 | 5.0 | — | — | — | — | — |
| Glycine | 1.0 | 1.0 | — | — | — | — | — |
| Citricidal | — | — | — | — | — | 1.0 | 1.0 |
| Perfume oil | — | — | 0.2 | 0.2 | — | — | — |
| Water | to 100 | to 100 | to 100 | to 100 | to 100 | to 100 | to 100 |

TABLE II

|  | 8 | 9 | 10 | 11 | 12 | 13 | 14 |
|---|---|---|---|---|---|---|---|
| Oil phase: | | | | | | | |
| Avocado oil | 10.0 | 10.0 | 10.0 | — | — | — | — |
| Heptamethyl nonane | 10.0 | 10.0 | 10.0 | — | — | — | 10.0 |
| Dow Corning 344 Fluid | — | — | — | 2.0 | — | — | — |
| Baysilonol M 350 | — | — | — | — | 2.0 | — | — |
| Abil-Wax 9801 | — | — | — | — | — | 2.0 | — |
| Microwax | — | 2.0 | — | — | — | — | — |
| Beeswax | 2.0 | — | — | — | — | — | — |
| Carnauba wax | — | — | 1.0 | — | — | — | — |
| Cetyl/stearyl alcohol | — | — | — | — | — | — | 2.0 |
| Lanette 22 | 6.0 | 6.0 | 6.0 | 6.0 | 6.0 | 6.0 | 4.0 |
| pHB propyl ester | 0.1 | 0.1 | 0.1 | 0.1 | — | — | — |
| Controx KS | 0.05 | 0.05 | 0.05 | 0.05 | — | — | — |
| Aqueous phase | | | | | | | |
| Na cetyl/stearyl sulfate | 0.1 | 0.1 | 0.1 | — | — | — | 0.1 |
| K cetyl hydrogen phosphate | — | — | — | 0.1 | 0.1 | 0.1 | — |
| Xanthan gum | 0.1 | 0.1 | 0.1 | 0.3 | 0.3 | 0.3 | 0.3 |
| Citricidal | 1.0 | 1.0 | 1.0 | — | — | — | — |
| Euxyl K 400 | — | — | — | — | 0.1 | — | — |
| Hexane-1,6-diol | — | — | — | 5.0 | — | — | — |
| Perfume oil | — | — | — | 0.2 | — | — | — |
| Water | 70.65 | 70.65 | 70.65 | 83.35 | 91.5 | 91.5 | 83.6 |

TABLE III

|  | 15 | 16 | 17 | 18 | 19 |
|---|---|---|---|---|---|
| Oil phase: | | | | | |
| Paraffin oil | — | — | 10.0 | — | 10.0 |
| Almond oil | — | — | — | 10.0 | — |
| Heptamethyl nonane | 10.0 | 6.7 | 10.0 | — | 10.0 |
| Decaglycerol decaoleate | — | 0.0 | — | — | — |
| Baysilonöl M 350 | — | — | 0.5 | — | — |
| Tocopherol acetate | — | 2.0 | — | — | — |
| Sorbitan monostearate | 2.0 | — | — | — | — |
| Arlacel 1689 | — | 1.0 | — | — | — |
| Biophilic S | — | — | 3.0 | — | — |
| Lanette 22 | 4.0 | 6.0 | 3.0 | 6.0 | 6.0 |
| pHB propyl ester | — | — | 0.1 | — | — |
| Controx KS | — | — | — | 0.05 | — |
| Aqueous phase | | | | | |
| Na cetyl/stearyl sulfate | 0.1 | — | — | — | — |
| K cetyl hydrogen phosphate | — | 0.15 | 0.1 | 0.1 | 0.1 |
| Xanthan gum | 0.3 | 0.1 | 0.3 | 0.1 | — |
| Dipropylene glycol | — | — | 3.0 | — | — |
| Glucose | — | 0.2 | — | — | — |
| Euxyl K 400 | — | — | 0.1 | 0.1 | 0.1 |
| Hexane-1,6-diol | — | 10.0 | — | — | — |
| Phenoxyethanol | — | — | 1.0 | — | — |
| Perfume | — | 0.2 | 0.2 | 0.2 | — |
| MgSO$_4$ | — | 0.2 | — | — | — |
| Water | 83.6 | | 68.7 | 83.55 | 73.8 |

TABLE IV

|  | 20 | V |
|---|---|---|
| Oil phase: | | |
| Paraffin oil | — | 10.0 |
| Isopropyl isostearate | 7.5 | — |
| Isopropyl palmitate | — | 5.0 |
| Almond oil | 5.0 | 2.0 |
| Night light oil | 2.0 | 2.0 |
| Baysilonol M 350 | 0.5 | — |
| Beeswax | — | 3.0 |
| Lanette 22 | 6.0 | — |
| Methyl glucose dioleate | — | 3.0 |
| Arlacel 989 | — | 0.1 |
| Soya sterol | — | 0.5 |
| Gilugel min | — | 3.0 |
| Tocopherol acetate | — | 2.0 |
| Controx KS | 0.05 | — |
| PHB propyl ester | 0.1 | 0.1 |
| Aqueous phase | | |
| Na cetyl/stearyl sulfate | 0.18 | — |
| Xanthan gum | 0.05 | — |
| Almond protein | 1.5 | 1.5 |
| Bisabolol | 0.1 | 0.1 |
| Glycolys | 1.0 | 1.0 |
| MgSO$_4$ | — | 1.0 |
| Glycerol | — | 1.0 |
| Propylene glycol | 3.0 | — |
| PHB methyl ester | 0.3 | 0.3 |
| Euxyl K 400 | 0.2 | 0.2 |
| Perfume oil | 0.37 | 0.37 |
| Water | 72.11 | 61.83 |

3. IR-spectroscopic Examination of the Effects on the Stratum Corneum

Test Data:

Test creams: cream no. 20 and w/o comparison cream C

Volunteers: two groups of 10 volunteers

Application: morning and evening to the forearm

Measurement: FT-IR-ATR, Zn Se crystal, left arm untreated (reference), right arm treated.

The measured data were determined by subtraction from the zero value.

Measuring times:

1.) zero value before the first application

2.) 12 h after the 28th application (2-week control)

A zero value for each arm was first determined using all the volunteers. The cream to be tested was then applied to the inside of the right forearm. This cream treatment was carried out morning and evening for 14 days. Differences between the measured values of the left arm (untreated) and right arm (treated) were determined. The mean values were calculated from these differences for each of the two groups of volunteers.

It was found that the position of the asymmetrical CH$_2$ stretching vibrational bands $v_{as}$ CH$_2$ in the group treated with cream No. 20 was 0.2 cm$^{-1}$ lower than the value for the untreated left forearm.

By contrast, in the group treated with a conventional w/o cream (formulation C), the position of the asymmetrical CH$_2$ stretching vibrational band $V_{as}$ CH$_2$ was 0.1 cm$^{-1}$ higher than the value for the untreated left arm.

The values were statistically significant at 95% probability.

The measurements suggest that the skin treated with cream No. 20 according to the invention has a higher degree of order, i.e. a lower percentage of higher-energy "gauche conformers", than the skin treated with the conventional w/o cream.

What is claimed is:

1. An oil-in-water emulsion comprising a lamellar liquid crystalline phase wherein the emulsion is free of salts of fat acids having at least 12 carbon atoms and comprises:

(a) a lipophilic co-emulsifier having the formula R$^1$—O—R$^2$, wherein R$^1$ is a primary linear alkyl or alkenyl group containing 20 to 30 carbon atoms and R$^2$ is hydrogen;

(b) a hydrophilic emulsifier, and (c) an oil phase comprising a cosmetic oil or a fatty component, wherein the oil phase comprises droplets comprising the cosmetic oil or fatty component and wherein the lamellar liquid crystalline phase surrounds the droplets and comprises the lipophilic co-emulsifier.

2. The oil-in-water emulsion of claim 1 comprising 10 to 90 percent by weight based on the oil phase of a behenic or erucyl alcohol as the lipophilic co-emulsifier.

3. The oil-in-water emulsion of claim 2 comprising 20 to 80 percent by weight of behenyl alcohol based on the oil phase, as the lipophilic co-emulsifier.

4. The oil-in-water emulsion of claim 1 wherein the hydrophilic emulsifier is an ionic or nonionic emulsifier with an HLB value of from 8 to 18.

5. A process for restoring the lamellarity and degree of order of the epidermal lipid structures of damaged skin comprising:

(a) forming an oil-in-water emulsion comprising a lamellar liquid crystalline phase, wherein the emulsion is free of salts of fatty acids having at least 12 carbon atoms and comprises:

(1) a lipophilic co-emulsifier having the formula R$^1$—O—R$^2$, wherein R$^1$ is a primary linear alkyl or alkenyl group contain 20 to 30 carbon atoms and R$^2$ is hydrogen;

(2) a hydrophilic emulsifier; and (3) an oil phase comprising a cosmetic oil or a fatty component, wherein the oil phase comprises droplets comprising the cosmetic oil or fatty component and wherein the lamellar liquid crystalline phase surrounds the droplets and comprises the lipophilic co-emulsifier; and (b) applying said oil-in-water emulsion to damaged skin.

6. A process for the production of oil-in-water emulsions for restoring the lamellarity and degree of order of the epidermal lipid structures of damaged skin comprising:

(a) forming an oil phase comprising a cosmetic oil or fatty component and a lipophilic co-emulsifier having the formula R$^1$—O—R$^2$, wherein R$^1$ is a primary alkyl or alkenyl group containing 20 to 30 carbon atoms and R$^2$ is hydrogen;

(b) heating said oil phase to a temperature at which it is present as a clear homogeneous melt;

(c) forming a aqueous phase comprising a hydrophilic emulsifier, (d) heating the aqueous phase to the same temperature as the oil phase;

(e) mixing the aqueous phase and oil phase intensively; and (f) lowering the temperature to below the phase inversion temperature of the emulsion to form an oil-in-emulsion comprising droplets containing the cosmetic oil or fatty component wherein the droplets are surrounded by a lamellar liquid crystalline phase comprising the lipophilic co-emulsifier and wherein the emulsion is free of salts of fatty acids having at least 12 carbon atoms.

* * * * *

UNITED STATES PATENT AND TRADEMARK OFFICE
CERTIFICATE OF CORRECTION

PATENT NO. : 6,379,681 B1
DATED : April 30, 2002
INVENTOR(S) : Bordat et al.

It is certified that error appears in the above-identified patent and that said Letters Patent is hereby corrected as shown below:

<u>Title page,</u>
Item [57], ABSTRACT, delete the ABSTRACT and insert therefore the following:
-- The present invention relates to an oil-in-water emulsion having a lamellar liquid crystalline phase. The oil-in-water emulsion contains a cosmetic oil or fatty component, a lipophilic co-emulsifier, and a hydrophilic emulsifier. The oil-in-water emulsion is particularly useful for restoring the lamellarity and degree of order of the epidermal lipid structures of damaged skin. --

<u>Column 8,</u>
Line 3, delete "fat" and insert therefore -- fatty --
Lines 9 and 54, delete "," and insert therefore -- ; --
Line 53, after "forming", delete "a", and insert therefore -- an --
Line 60, delete "oil-in-emulsion", and insert therefore -- oil-in-water emulsion --.

Signed and Sealed this

Second Day of August, 2005

JON W. DUDAS
*Director of the United States Patent and Trademark Office*